(12) United States Patent
Ejike et al.

(10) Patent No.: US 9,011,383 B2
(45) Date of Patent: Apr. 21, 2015

(54) SELF-ILLUMINATING ENDOGASTRIC TUBES AND METHOD OF PLACING ENDOGASTRIC TUBES

(75) Inventors: Janeth C. Ejike, Highland, CA (US); Shamel Abd-Allah, Rancho Cucamonga, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 13/350,687

(22) Filed: Jan. 13, 2012

(65) Prior Publication Data

US 2012/0184924 A1   Jul. 19, 2012

Related U.S. Application Data

(60) Provisional application No. 61/432,947, filed on Jan. 14, 2011.

(51) Int. Cl.
| | | |
|---|---|---|
| *A61M 5/178* | (2006.01) | |
| *A61M 31/00* | (2006.01) | |
| *B01J 20/20* | (2006.01) | |
| *A61M 39/08* | (2006.01) | |
| *B09B 3/00* | (2006.01) | |
| *A01G 1/00* | (2006.01) | |

(Continued)

(52) U.S. Cl.
CPC ............... *B01J 20/20* (2013.01); *A61M 39/08* (2013.01); *B09B 3/0083* (2013.01); *C02F 11/04* (2013.01); *A01G 1/001* (2013.01); *B01D 53/04* (2013.01); *B01J 20/3085* (2013.01); *Y02C 10/08* (2013.01); *C05F 17/0027* (2013.01); *Y02C 20/20* (2013.01); *Y02E 50/346* (2013.01); *B01J 20/3078* (2013.01)

(58) Field of Classification Search
CPC ...... A61B 1/06; A61B 1/0607; A61B 1/0615; A61B 1/0684; A61B 1/07
USPC ................. 600/478; 604/170.01–170.03, 270
See application file for complete search history.

(56) References Cited

U.S. PATENT DOCUMENTS

4,516,970 A * 5/1985 Kaufman et al. ............. 604/270
4,567,882 A * 2/1986 Heller ........................... 600/249

(Continued)

FOREIGN PATENT DOCUMENTS

WO   WO 0219890 A2 *  3/2002
WO   WO 2006/049787     5/2006

(Continued)

*Primary Examiner* — Theodore Stigell
*Assistant Examiner* — Benjamin Koo
(74) *Attorney, Agent, or Firm* — Knobbe Martens Olson & Bear LLP

(57) ABSTRACT

A self-illuminating endogastric tube which simplifies the correct placement of the distal end of the endogastric tube within the gastrointestinal tract of a patient. A self-illuminating stylet which simplifies the correct placement of the distal end of an endogastric tube within the gastrointestinal tract of a patient. A method of placing the distal end of an endogastric tube within the gastrointestinal tract of a patient that does not expose the patient to radiation, or that limits the amount of radiation exposure to less than the amount associated with standard methods of placing the distal end of an endogastric tube within the gastrointestinal tract of a patient. A method of confirming the correct placement of an endogastric tube that does not expose the patient to radiation, or that limits the amount of radiation exposure to less than the amount associated with standard methods of placing an endogastric tube.

18 Claims, 10 Drawing Sheets

(51) Int. Cl.
  *B01D 53/04* (2006.01)
  *B01J 20/30* (2006.01)
  *C05F 17/00* (2006.01)
  *C02F 11/04* (2006.01)

(56) References Cited

U.S. PATENT DOCUMENTS

| | | | |
|---|---|---|---|
| 5,370,640 A * | 12/1994 | Kolff | 606/2 |
| 5,507,284 A | 4/1996 | Daneshvar | |
| 6,929,600 B2 * | 8/2005 | Hill | 600/120 |
| 7,757,695 B2 * | 7/2010 | Wilson et al. | 128/899 |
| 7,917,193 B2 * | 3/2011 | Crane | 600/476 |
| 7,992,573 B2 | 8/2011 | Wilson et al. | |
| 8,465,479 B2 * | 6/2013 | Whayne et al. | 606/14 |
| 8,613,702 B2 | 12/2013 | Feer et al. | |
| 8,677,990 B2 * | 3/2014 | Gabriel | 128/200.26 |
| 2003/0154986 A1 * | 8/2003 | Fariss et al. | 128/207.14 |
| 2004/0093044 A1 * | 5/2004 | Rychnovsky et al. | 607/88 |
| 2006/0036164 A1 * | 2/2006 | Wilson et al. | 600/424 |
| 2008/0039715 A1 | 2/2008 | Wilson et al. | |
| 2008/0146874 A1 * | 6/2008 | Chen | 600/109 |
| 2008/0194973 A1 * | 8/2008 | Imam | 600/478 |
| 2010/0305503 A1 * | 12/2010 | Fang et al. | 604/96.01 |
| 2012/0204866 A1 | 8/2012 | Kizer | |
| 2013/0046172 A1 | 2/2013 | Waitzman et al. | |
| 2013/0225946 A1 | 8/2013 | Feer et al. | |

FOREIGN PATENT DOCUMENTS

| | | |
|---|---|---|
| WO | WO 2008/154533 | 12/2008 |
| WO | WO 2010/023579 | 3/2010 |
| WO | WO 2013/066653 | 5/2013 |

* cited by examiner

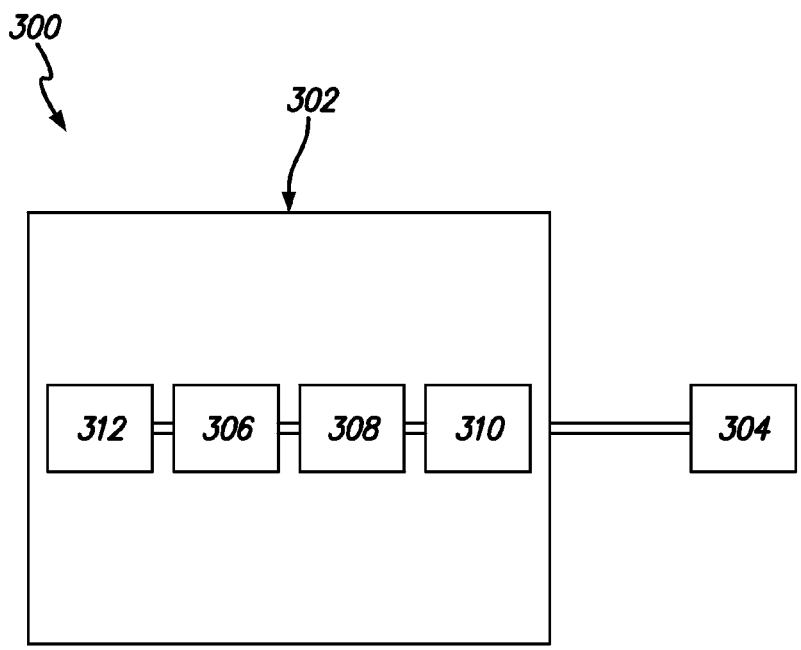
FIG. 13
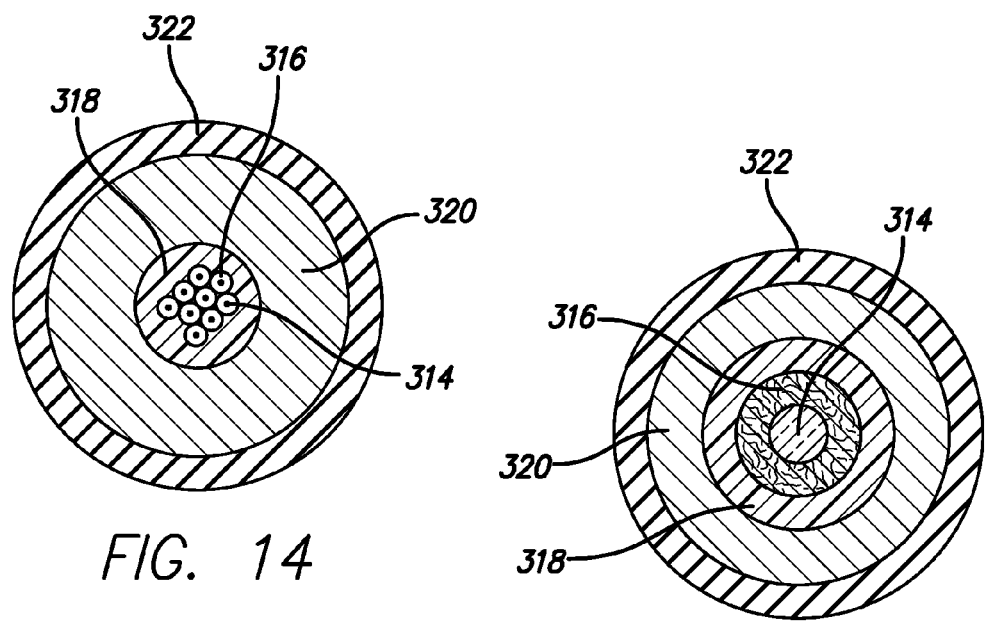
FIG. 14
FIG. 15

SELF-ILLUMINATING ENDOGASTRIC TUBES AND METHOD OF PLACING ENDOGASTRIC TUBES

CROSS-REFERENCE TO RELATED APPLICATION

The present application claims the benefit of U.S. Provisional Patent Application No. 61/432,947, titled "Self-Illuminating Endogastric Tubes and Method of Placing Endogastric Tubes," filed Jan. 14, 2011, the contents of which are incorporated in this disclosure by reference in their entirety.

Endogastric tubes, such as for example nasogastric tubes and orogastric tubes, are placed through the nasal passage or oral cavity, respectively, and into the gastrointestinal tract of a patient as a conduit for introducing or removing substances into or from the gastrointestinal tract of the patient. Endogastric tubes are particularly useful in the treatment of patients who cannot take nutrition orally such as patients with compromised mentation or defects in swallowing.

BACKGROUND

Endogastric tubes are placed by inserting the distal end of the endogastric tube into the nasal passage or oral cavity of the patient and advancing the distal end of the endogastric tube into the gastrointestinal tract of a patient. Commonly, the distal end of the endogastric tube is advanced until the distal end of the endogastric tube is in the stomach; however, the distal end of the endogastric tube can be advanced until the distal end of the endogastric tube is more distal in the gastrointestinal tract. Alternately, a stylet is advanced until the distal end of the stylet is in the stomach or is more distal in the gastrointestinal tract, the endogastric tube is advanced over the stylet until the distal end of the endogastric tube is in the stomach or is more distal in the gastrointestinal tract, and the stylet is removed leaving the distal end of the endogastric tube in the desired location within the gastrointestinal tract. Once the distal end of the endogastric tube is placed, determination of correct placement or incorrect placement is made using radiography, such as for example an abdominal x-ray or fluoroscopy.

While generally effective, this method of placing an endogastric tube is disadvantageously associated with various complications, including incorrect placement of the distal end of the endogastric tube into the trachea or bronchial tree with the development of hemothorax, pneumonia or pneumothorax, penetration of the esophagus, or incorrect placement of the distal end of the endogastric tube into the cranial cavity (when placement is associated with basal skull fractures) and mediastinitis. Additionally, determination of correct placement or incorrect placement by radiography exposes the patient to significant radiation with the inherent long-term risks of radiation exposure. Further, endogastric tubes can move from their original location after an initial determination of correct placement. Therefore, repeated radiographic confirmation of the placement of the distal end of the endogastric tube is required, increasing the amount of radiation exposure and inherent long-term risks of radiation exposure.

Therefore, there is a need for a new endogastric tube and a new method of placing an endogastric tube that are not associated with these disadvantages.

SUMMARY

According to one embodiment of the present invention, there is provided a self-illuminating endogastric tube comprising: a) a tubular body comprising a proximal end and a distal end, and extending between the proximal end and the distal end respectively, a proximal section continuous with an intermediate section continuous with a distal section; b) an outer surface and an opposing inner surface defining a tubular wall between the outer surface and the inner surface, where the tubular wall extends from the proximal section to the distal section; c) a central lumen defined and externally bounded by the inner surface, where the central lumen extends from an administration port in the proximal section at the proximal end of the self-illuminating endogastric tube to a distal opening in the distal section of the self-illuminating endogastric tube; and d) one or more than one light transmitting element within the tubular wall; where the intermediate section comprises the tubular body and connects the proximal section to the distal section of the self-illuminating endogastric tube; where the distal section of the self-illuminating endogastric tube comprises a light transmitting section, where the outer surface and at least part of the thickness of the tubular wall is transparent or translucent sufficient to allow light from the one or more than one light transmitting element within the tubular wall to traverse the tubular wall; where the distal section further comprises a distal opening in communication with the central lumen; and where each light transmitting element extends from the proximal section of the self-illuminating endogastric tube within the tubular wall and terminates within the light transmitting section of the distal end of the self-illuminating endogastric tube.

In one embodiment, the self-illuminating endogastric tube is selected from the group consisting of a self-illuminating enteric tube, a self-illuminating nasogastric tube and a self-illuminating orogastric tube. In another embodiment, the proximal end of the self-illuminating endogastric tube is an adapter for mating with a light supplying source. In another embodiment, the proximal section of the self-illuminating endogastric tube further comprises a side extension comprising an accessory lumen comprising a proximal end of the accessory lumen and a distal end of the accessory lumen, where the proximal end of the accessory lumen is in communication externally to the environment, and the distal end of the accessory lumen is in communication with the central lumen. In another embodiment, the proximal section further comprises a cap connected to the outer surface for sealing the accessory lumen. In another embodiment, the proximal section further comprises a catheter tip adapter connected to the outer surface. In another embodiment, the proximal section further comprises a flow-through stylet connector removably connected to the proximal end of the self-illuminating endogastric tube. In another embodiment, the proximal section further comprises an adapter for a light transmitting conduit removably connected to the proximal end of the self-illuminating endogastric tube. In another embodiment, the intermediate section of the self-illuminating endogastric tube comprises markings on the outer surface denoting distances along the length of the self-illuminating endogastric tube. In another embodiment, at least 80% of the thickness of the tubular wall is transparent or translucent sufficient to allow light from the one or more than one light transmitting element within the tubular wall to traverse the tubular wall. In another embodiment, the distal section further comprises a weighted tip at the distal end of the self-illuminating endogastric tube. In another embodiment, the light transmitting section is proximal to the distal opening. In another embodiment, the light transmitting section is distal to the distal opening. In another embodiment, the light transmitting section is coincident with the distal opening. In another embodiment, the one or more than one light transmitting element is three light transmitting elements. In another embodiment, each light transmitting element is an optical fiber or is a cable of optic fibers. In another embodiment, the self-illuminating endogastric tube further comprises a light supplying source connected to the self-illuminating endogastric tube.

According to another embodiment of the present invention, there is provided a self-illuminating stylet used for placing an endogastric tube, the self-illuminating stylet comprising: a) a cylindrical body comprising a proximal end and a distal end, and extending between the proximal end and the distal end respectively, a proximal section continuous with an intermediate section continuous with a distal section; and b) one or more than one light transmitting element; where each light transmitting element extends from the proximal section of the self-illuminating stylet within the cylindrical body and terminates within the light transmitting section of the distal section of the self-illuminating stylet; where the proximal section of the self-illuminating stylet comprises an adapter for mating with a light supplying source; where the distal section of the self-illuminating stylet comprises a light transmitting section, where the cylindrical body is transparent or translucent sufficient to allow light from the one or more than one light transmitting element within the cylindrical body to traverse the cylindrical body; and where each light transmitting element extends from the proximal section of the self-illuminating stylet within the cylindrical body and terminates within the light transmitting section of the distal section of the self-illuminating stylet.

In one embodiment, the cylindrical body comprises transparent polyurethane, or comprises polyvinylchloride. In another embodiment, the proximal section of the self-illuminating stylet further comprises a lens for focusing light from a light supplying source to the light transmitting element or light transmitting elements within the self-illuminating stylet. In another embodiment, the one or more than one light transmitting elements is three light transmitting elements. In another embodiment, each light transmitting element is an optical fiber or a cable of optic fibers. In another embodiment, the self-illuminating stylet further comprises a light supplying source connected to the self-illuminating endogastric tube.

According to another embodiment of the present invention, there is provided a method of placing an endogastric tube. The method comprises: a) selecting a patient who has a need that will be met by placement of an endogastric tube; b) providing a self-illuminating endogastric tube according to the present invention; c) inserting the distal end of the self-illuminating endogastric tube through a nasal passage or oral cavity of the patient and into the gastrointestinal tract of the patient; d) supplying light to the one or more than one light transmitting element of the self-illuminating endogastric tube, causing light to be transmitted to the light transmitting section of the distal end of the self-illuminating endogastric tube; and e) examining the abdominal wall and the chest wall of the patient to identify and locate the light from the one or more than one light transmitting element as the light passes through the body wall of the patient; where light appearing between the costal border and the umbilicus of the patient indicates placement of the distal end of the self-illuminating endogastric tube within the gastrointestinal tract of the patient; where light appearing superior to the costal border indicates incorrect placement of the distal end of the self-illuminating endogastric tube outside of the gastrointestinal tract of the patient; and where failure to identify light passing through the body wall of the patient indicates failure to confirm correct placement of the distal end of the self-illuminating endogastric tube.

According to another embodiment of the present invention, there is provided a method of placing an endogastric tube. The method comprises: a) selecting a patient who has a need that will be met by placement of an endogastric tube; b) providing a self-illuminating stylet according to the present invention; c) inserting the distal end of the self-illuminating stylet through a nasal passage or oral cavity of the patient and into the gastrointestinal tract of the patient; d) supplying light to the one or more than one light transmitting element of the self-illuminating stylet, causing light to be transmitted to the light transmitting section of the distal end of the self-illuminating stylet; and e) examining the abdominal wall and the chest wall of the patient to identify and locate the light from the one or more than one light transmitting element as the light passes through the body wall of the patient; where light appearing between the costal border and the umbilicus of the patient indicates placement of the distal end of the self-illuminating stylet within the gastrointestinal tract of the patient; where light appearing superior to the costal border indicates incorrect placement of the distal end of the self-illuminating stylet outside of the gastrointestinal tract of the patient; and where failure to identify light passing through the body wall of the patient indicates failure to confirm correct placement of the distal end of the self-illuminating stylet.

According to another embodiment of the present invention, there is provided a method of reconfirming the position of a self-illuminating endogastric tube according to the present invention. The method comprises: a) supplying light to the one or more than one light transmitting element of the self-illuminating endogastric tube; and b) detecting the position of the distal end of the endogastric tube.

According to the present invention, there is provided a method of reconfirming the position of an endogastric tube, the endogastric tube comprising a distal end. The method comprises: a) inserting a self-illuminating stylet according to the present invention; b) advancing the distal end of the self-illuminating stylet to the distal end of the endogastric tube; c) supplying light to the one or more than one light transmitting element of the self-illuminating stylet; d) detecting the position of the distal end of the endogastric tube.

According to the present invention, there is provided a kit comprising a) a self-illuminating endogastric tube according to the present invention, and b) a self-illuminating stylet according to the present invention.

FIGURES

These and other features, aspects and advantages of the present invention will become better understood with regard to the following description, appended claims, and accompanying figures where:

FIG. 1 is a lateral perspective view of a self-illuminating endogastric tube according to the present invention;

FIGS. 2a, 2b, and 2c are close-up, partial, lateral perspective views of the self-illuminating endogastric tube shown in FIG. 1;

FIG. 13 is a schematic view of some of the parts of the light supplying source shown in FIG. 12;

FIG. 14 is a close-up, cross-sectional view of one embodiment of the light transmitting cable of the light supplying source shown in FIG. 12 and FIG. 13 taken through line 14-14; and FIG. 15 is a close-up, cross-sectional perspective view of another embodiment of the light transmitting cable of the light supplying source shown in FIG. 12 and FIG. 13 taken through line 15-15.

DESCRIPTION

Figure 1:
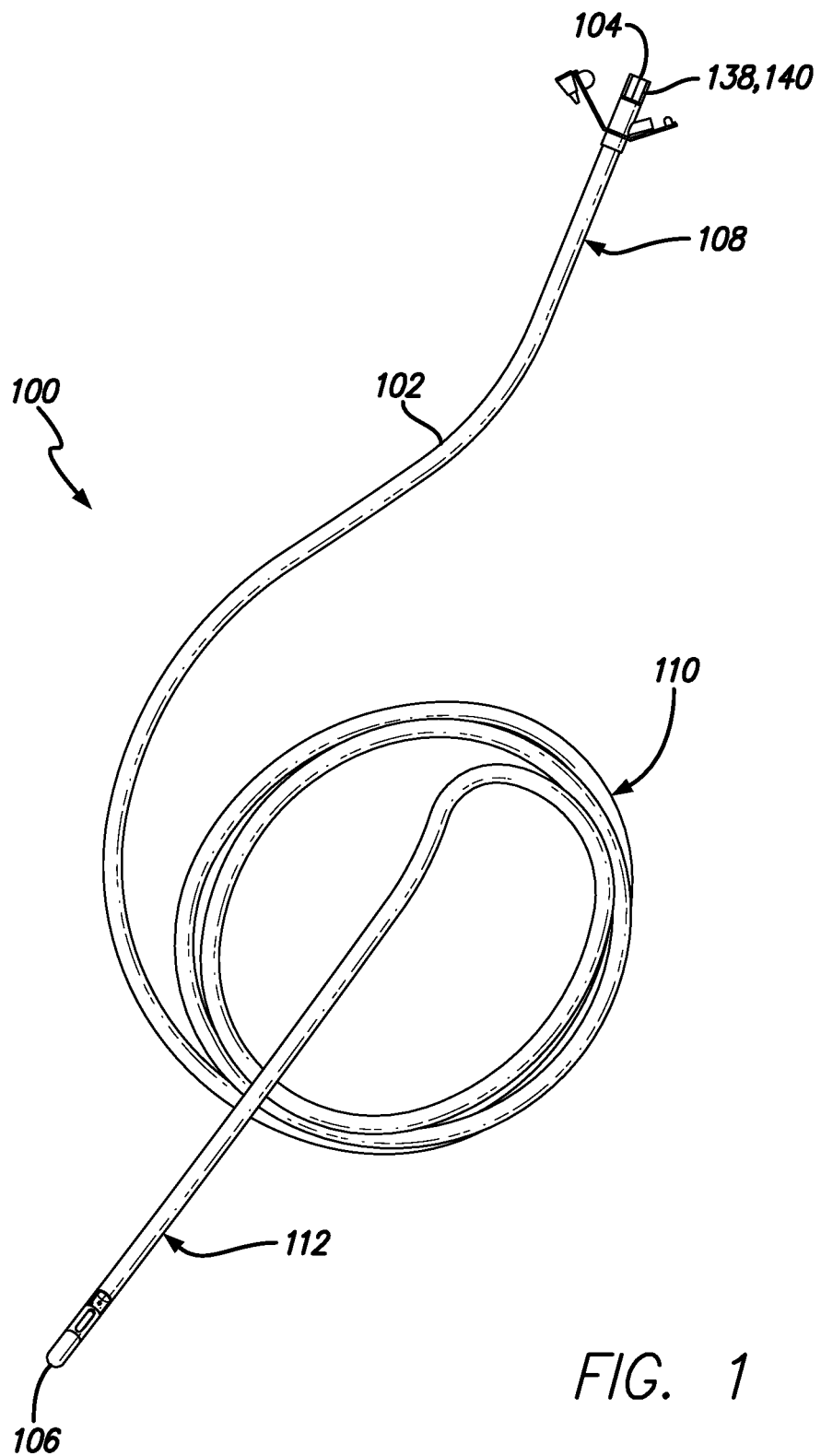

According to one embodiment of the present invention, there is provided a self-illuminating endogastric tube which simplifies the correct placement of the distal end of the endogastric tube within the gastrointestinal tract of a patient. According to another embodiment of the present invention, there is provided a self-illuminating stylet used for placing the distal end of an endogastric tube within the gastrointestinal tract of a patient. According to another embodiment of the present invention, there is provided a kit for placing the distal end of an endogastric tube within the gastrointestinal tract of a patient, where the kit comprises a self-illuminating stylet, or comprises a self-illuminating endogastric tube, or comprises both a self-illuminating stylet and a self-illuminating endogastric tube. According to another embodiment of the present invention, there is provided a method of placing the distal end of an endogastric tube within the gastrointestinal tract of a patient that does not expose the patient to ionizing radiation, or that limits the amount of ionizing radiation exposure to less than the amount associated with standard methods of placing the distal end of an endogastric tube within the gastrointestinal tract of a patient. The method comprises providing a self-illuminating stylet according to the present invention, or comprises providing a self-illuminating endogastric tube according to the present invention, or comprises providing both a self-illuminating stylet and a self-illuminating endogastric tube according to the present invention. According to another embodiment of the present invention, there is provided a method of confirming the correct placement of an endogastric tube that does not expose the patient to ionizing radiation, or that limits the amount of ionizing radiation exposure to less than the amount associated with standard methods of placing an endogastric tube. Additionally, the endogastric tube, stylet and methods can be used where radiographic confirmation of placement is inconvenient or is not possible. The self-illuminating endogastric tube, self-illuminating stylet and methods will now be disclosed in detail.

As used in this disclosure, the term "endogastric tube" includes any tube intended for placement within the gastrointestinal tract of a patient, such as for example an enteric tube, a nasogastric tube and an orogastric tube, as will be understood by those with skill in the art with reference to this disclosure.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any device or part of a device disclosed in this disclosure will be determined by its intended use.

The devices of the present invention and their component parts comprise any suitable material for the intended purpose of the device, as will be understood by those with skill in the art with reference to this disclosure. For example, the self-illuminating endogastric tube and self-illuminating stylet will comprise one or more than one biocompatible material. In one embodiment, the material is capable of being sterilized between uses to permit multiple uses of the devices.

The devices of the present invention and their component parts can be constructed according to standard techniques, as will be understood by those with skill in the art with reference to this disclosure.

Figure 6:
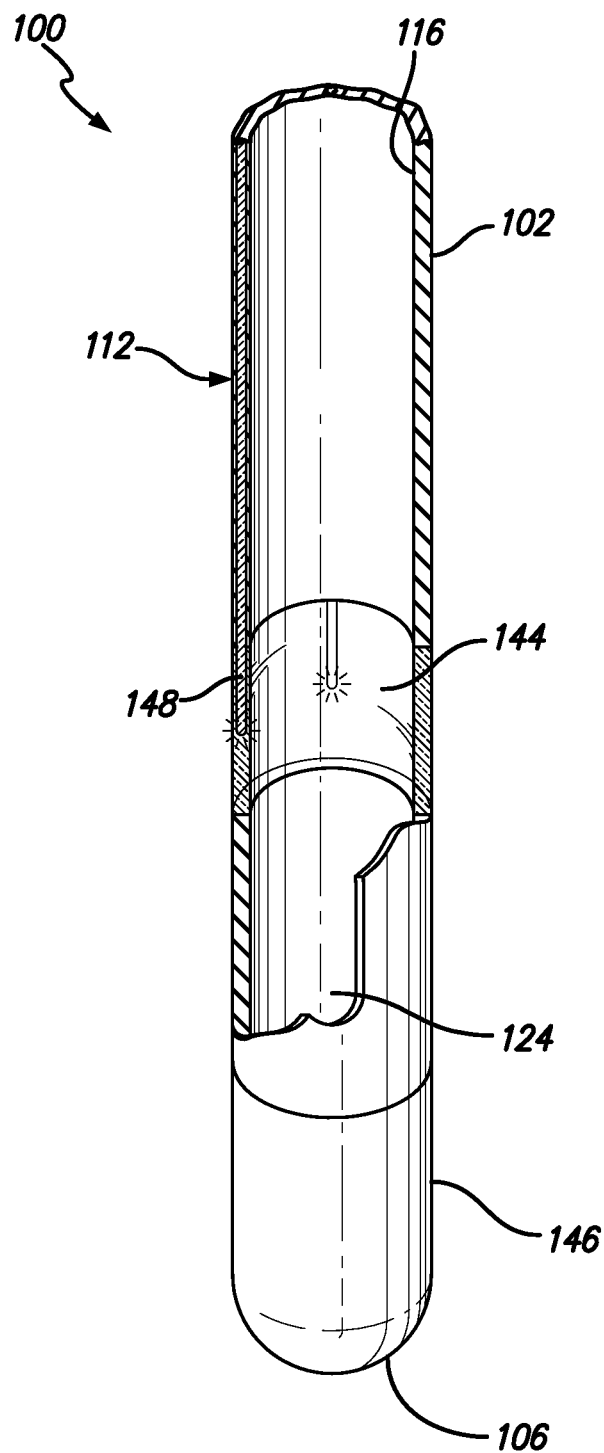
FIG. 6 is a cutaway, close-up, partial, lateral perspective view of the distal section of the self-illuminating endogastric tube shown in FIG. 1 and FIG. 2a taken through line 6-6.

According to one embodiment of the present invention, there is provided a self-illuminating endogastric tube used for placing the distal end of the self-illuminating endogastric tube within the gastrointestinal tract of a patient. In one embodiment, the self-illuminating endogastric tube is a self-illuminating enteric tube. In another embodiment, the self-illuminating endogastric tube is a self-illuminating nasogastric tube. In another embodiment, the self-illuminating endogastric tube is a self-illuminating orogastric tube. Referring now to FIG. 1 through FIG. 6, there are shown, respectively, a lateral perspective view of a self-illuminating endogastric tube according to the present invention (FIG. 1); close-up, partial, lateral perspective views of the self-illuminating endogastric tube shown in FIG. 1 FIGS. 2a, 2b and 2c); a cutaway, close-up, partial, lateral perspective view of the proximal section of the self-illuminating endogastric tube shown in FIG. 1 and FIG. 2a taken through line 3-3 (FIG. 3); a close-up, cross-sectional perspective view of the proximal section of the self-illuminating endogastric tube shown in FIG. 1 and FIG. 2a taken through line 4-4 (FIG. 4); a cutaway, close-up, partial, lateral perspective view of the intermediate section of the self-illuminating endogastric tube shown in FIG. 1 and FIG. 2a taken through line 5-5 (FIG. 5); and a cutaway, close-up, partial, lateral perspective view of the distal section of the self-illuminating endogastric tube shown in FIG. 1 and FIG. 2a taken through line 6-6 (FIG. 6). As can be seen, in one embodiment, the self-illuminating endogastric tube 100 comprises a tubular body 102 comprising a proximal end 104 and a distal end 106, and extending between the proximal end 104 and the distal end 106 respectively, a proximal section 108 continuous with an intermediate section 110 continuous with a distal section 112. The self-illuminating endogastric tube 100 further comprises an outer surface 114 and an opposing inner surface 116 defining a tubular wall 118 between the outer surface 114 and the inner surface 116, where the tubular wall 118 extends from the proximal section 108 to the distal section 112. The self-illuminating endogastric tube 100 further comprises a central lumen 120 defined and externally bounded by the inner surface 116, where the central lumen 120 extends from an administration port 122 in the proximal section 108 at the proximal end 104 of the self-illuminating endogastric tube 100 to a distal opening 124 in the distal section 112 of the self-illuminating endogastric tube 100 as shown particularly in FIG. 2a and FIG. 6.

In one embodiment, the proximal end 104 of the self-illuminating endogastric tube 100 is an adapter for mating with a light supplying source. As can be seen particularly in FIG. 3 and FIG. 4, the proximal end 104 is a female form adapter; however, other configurations are also possible, as will be understood by those with skill in the art with reference to this disclosure.

In one embodiment, the proximal section 108 of the self-illuminating endogastric tube 100 further comprises a side extension 126 comprising an accessory lumen 128, such as for example a flushing or medication delivery lumen, where the accessory lumen 128 comprises a proximal end 130 and a distal end 132, where the proximal end 130 of the accessory lumen 128 is in communication externally to the environment, and the distal end 132 of the accessory lumen 128 is in communication with the central lumen 120. In another embodiment, the proximal section 108 further comprises a cap 134 connected to the outer surface 114 for sealing the accessory lumen 128. In another embodiment, the proximal section 108 further comprises a catheter tip adapter 136 connected to the outer surface 114. In a preferred embodiment, the proximal section 108 further comprises a flow-through stylet connector 138 removably connected to the proximal end 104 of the self-illuminating endogastric tube 100. In another preferred embodiment, the proximal section 108 further comprises an adapter 140 for a light transmitting conduit removably connected to the proximal end 104 of the self-illuminating endogastric tube 100.

The intermediate section 110 comprises the tubular body 102 and connects the proximal section 108 to the distal section 112 of the self-illuminating endogastric tube 100. In one embodiment, the intermediate section 110 of the self-illuminating endogastric tube 100 comprises markings 142 on the outer surface 114 denoting distances along the length of the self-illuminating endogastric tube 100. In a preferred embodiment, the markings 142 are spaced one centimeter apart.

The distal section 112 of the self-illuminating endogastric tube 100 comprises a light transmitting section 144, where the outer surface 114 and at least part of the thickness of the tubular wall 118 is transparent or translucent sufficient to allow light from the one or more than one light transmitting element within the tubular wall 118 to traverse the tubular wall, and thereby to be detected, as will be understood by those with skill in the art with reference to this disclosure. In one embodiment, at least 20% of the thickness of the tubular wall 118 is transparent or translucent sufficient to allow light from the one or more than one light transmitting element within the tubular wall 118 to be detected, as will be understood by those with skill in the art with reference to this disclosure. In one embodiment, at least 50% of the thickness of the tubular wall 118 is transparent or translucent sufficient to allow light from the one or more than one light transmitting element within the tubular wall 118 to be detected, as will be understood by those with skill in the art with reference to this disclosure. In one embodiment, at least 80% of the thickness of the tubular wall 118 is transparent or translucent sufficient to allow light from the one or more than one light transmitting element within the tubular wall 118 to be detected, as will be understood by those with skill in the art with reference to this disclosure. In one embodiment, 100% of the thickness of the tubular wall 118 is transparent or translucent sufficient to allow light from the one or more than one light transmitting element within the tubular wall 118 to be detected, as will be understood by those with skill in the art with reference to this disclosure.

Figure 2A:
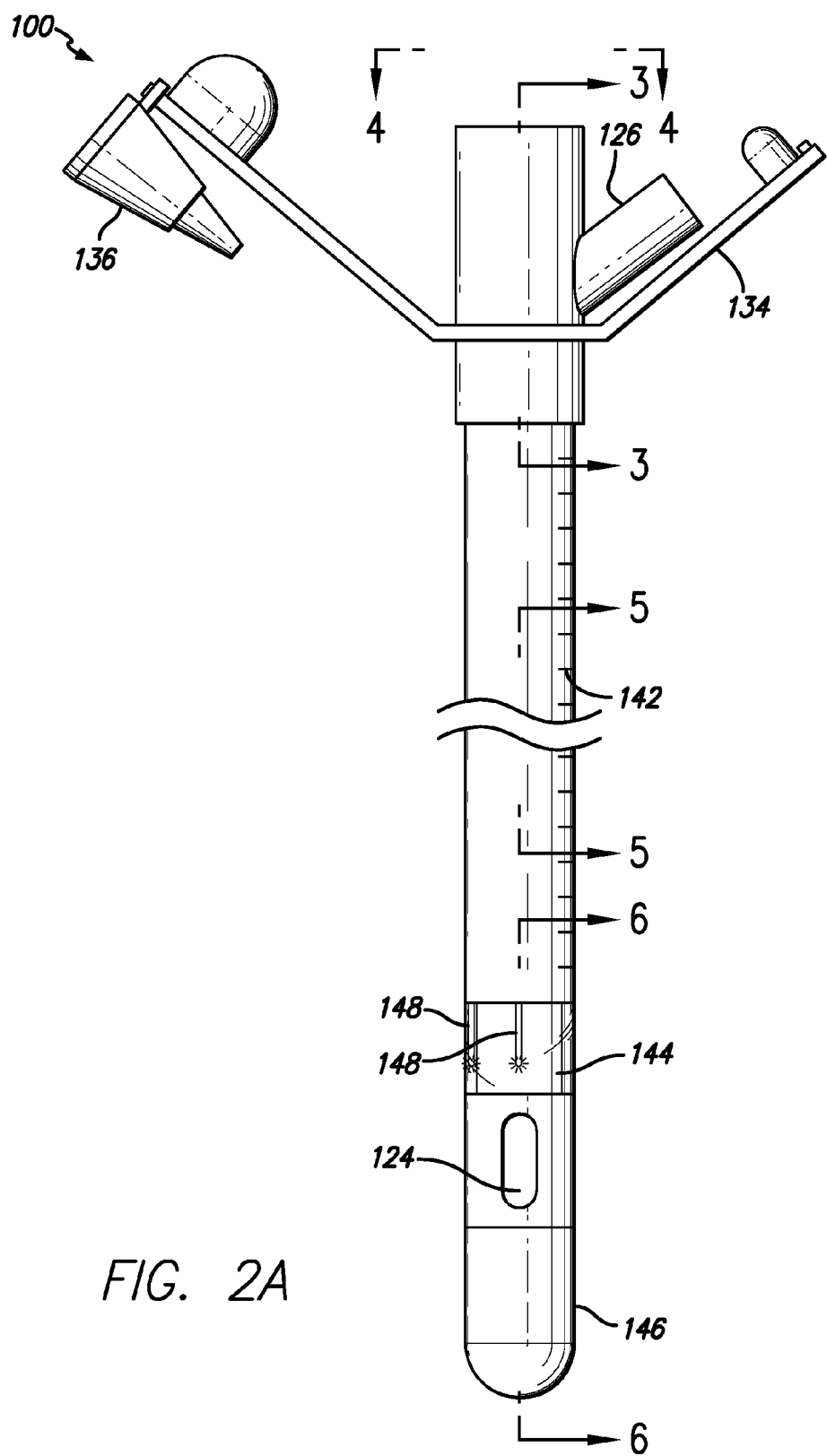
Figure 2B:
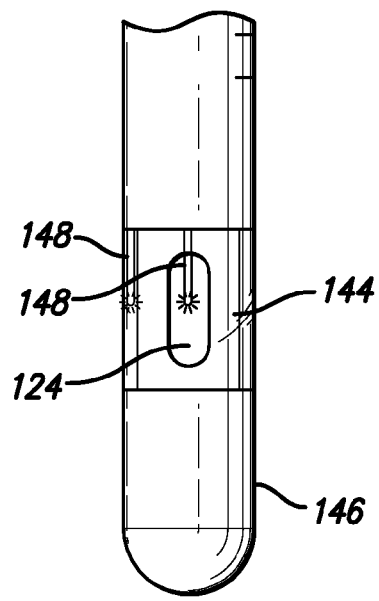
Figure 2C:
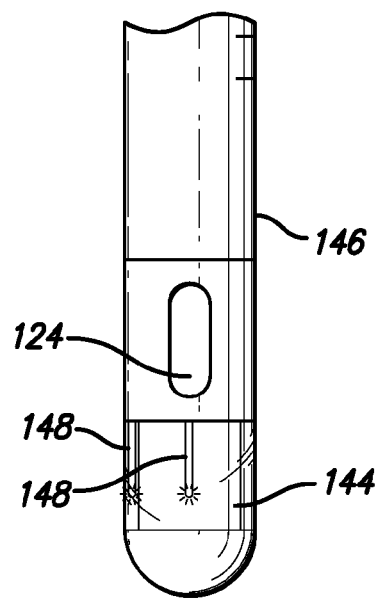
Figure 3:
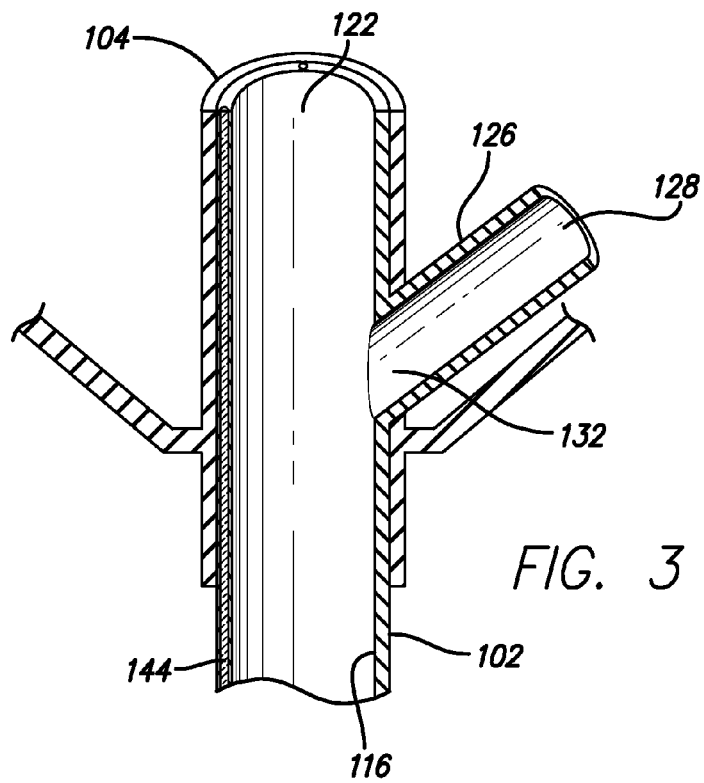
FIG. 3 is a cutaway, close-up, partial, lateral perspective view of the proximal section of the self-illuminating endogastric tube shown in FIG. 1 and FIG. 2a taken through line 3-3.
Figure 4:
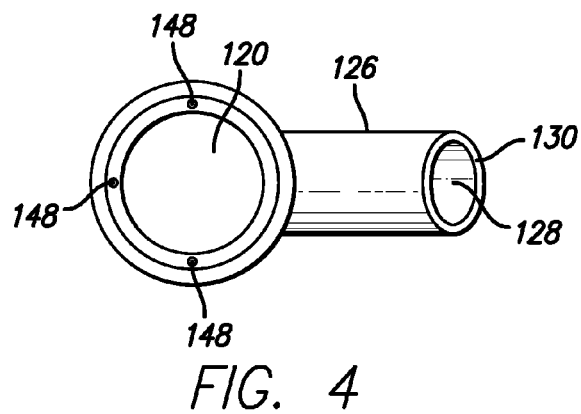
FIG. 4 is a close-up, cross-sectional perspective view of the proximal section of the self-illuminating endogastric tube shown in FIG. 1 and FIG. 2a taken through line 4-4.
Figure 5:
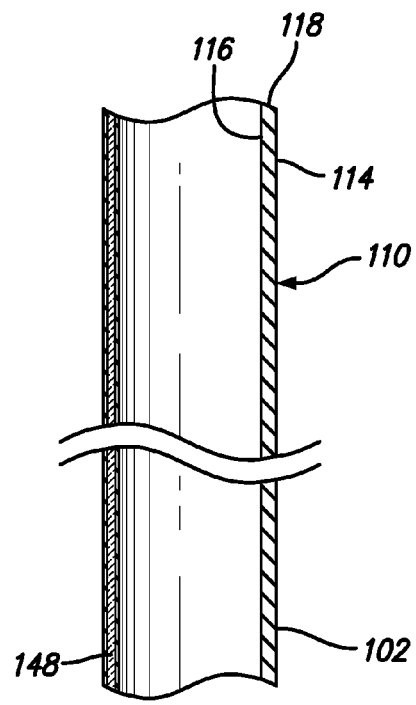
FIG. 5 is a cutaway, close-up, partial, lateral perspective view of the intermediate section of the self-illuminating endogastric tube shown in FIG. 1 and FIG. 2a taken through line 5-5.

The distal section 112 further comprises a distal opening 124 in communication with the central lumen 120. In a preferred embodiment, the distal section 112 further comprises a weighted tip 146 at the distal end 106 of the self-illuminating endogastric tube 100. The light transmitting section 144 can be proximal to the distal opening 124, as shown particularly in FIG. 2a and FIG. 6, can be distal to the distal opening 124 as shown in FIG. 2c, particularly when the self-illuminating endogastric tube 100 does not have a weighted distal end 106, or can be coincident with the distal opening 124 as shown in Fig. 2b.

The self-illuminating endogastric tube 100 further comprises one or more than one light transmitting element 148 within the tubular wall 118. In one embodiment, the self-illuminating endogastric tube 100 comprises one light transmitting element 148. In another embodiment, the self-illuminating endogastric tube 100 comprises two light transmitting elements 148. In another embodiment, the self-illuminating endogastric tube 100 comprises three light transmitting elements 148. In another embodiment, the self-illuminating endogastric tube 100 comprises more than three light transmitting elements 148. Each light transmitting element 148 extends from the proximal section 108 of the self-illuminating endogastric tube 100 within the tubular wall 118 and terminates within the light transmitting section 144 of the distal end 106 of the self-illuminating endogastric tube 100, as shown particularly in FIG. 2a, 2b, 2c and FIG. 6. In a preferred embodiment, each light transmitting element 148 is an optical fiber or is a cable of optic fibers; however, the self-illuminating endogastric tube 100 can comprise any suitable light transmitting element 148, as will be understood by those with skill in the art with reference to this disclosure.

Figure 10:
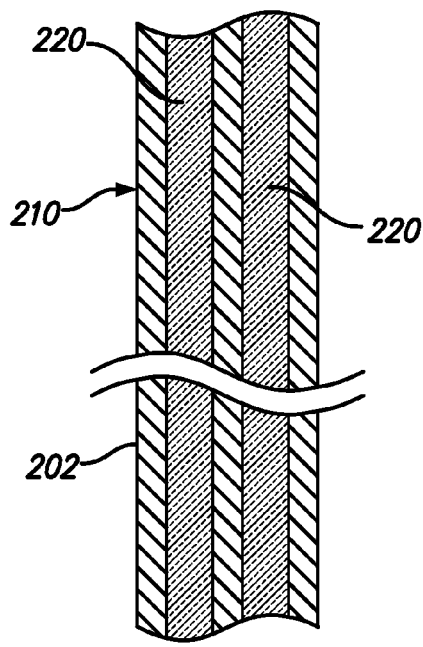
FIG. 10 is a close-up, partial, longitudinal sectional, perspective view of another embodiment of the intermediate section of the self-illuminating stylet shown in FIG. 7 taken through line 10-10 comprising two light transmitting elements.
Figure 11:
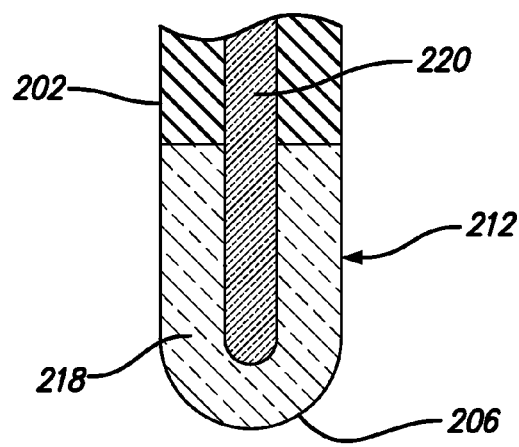
FIG. 11 is a close-up, partial, longitudinal sectional, perspective view of one embodiment of the distal section of the self-illuminating stylet shown in FIG. 7 and FIG. 9 taken through line 11-11 comprising one light transmitting element.
Figure 12:
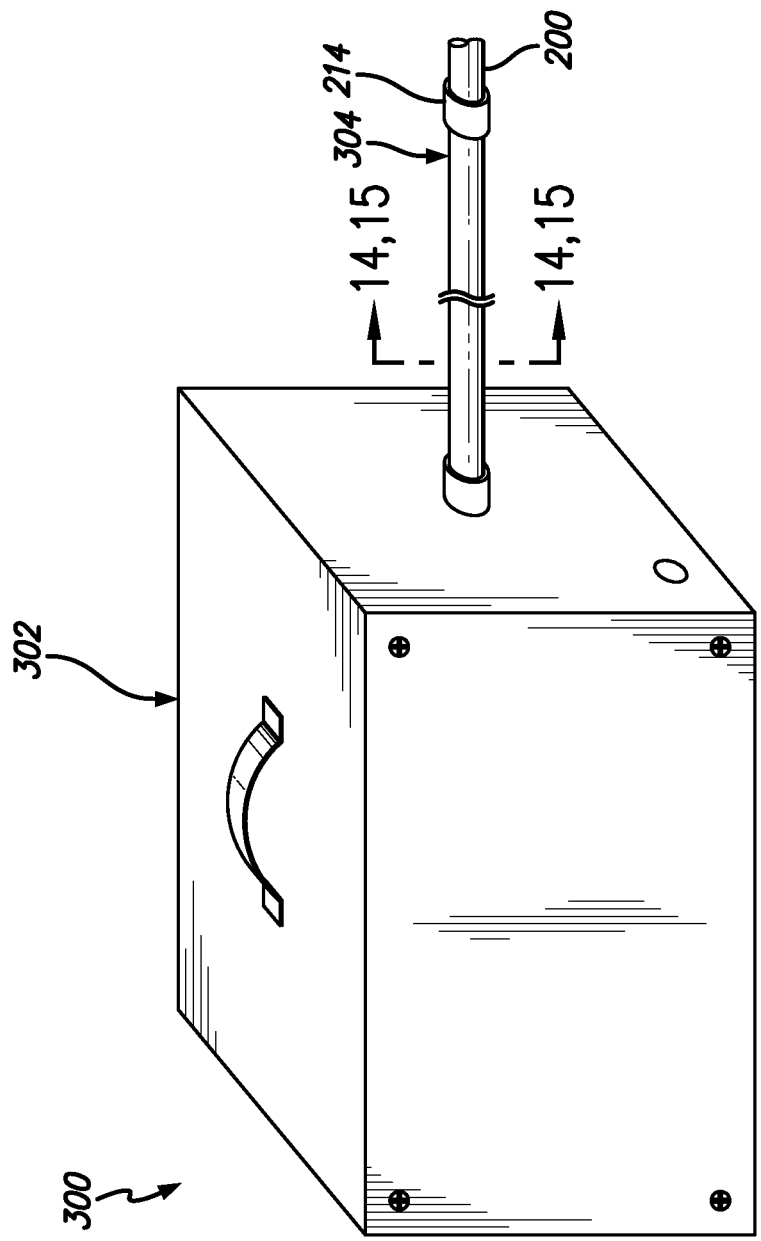
FIG. 12 is a lateral perspective view of a light supplying source according to the present invention.

According to another embodiment of the present invention, there is provided a self-illuminating stylet used for placing an endogastric tube. Referring now to FIG. 7, FIG. 8, FIG. 9, FIG. 10 and FIG. 11, there are shown, respectively, a close-up, partial, lateral perspective view of the self-illuminating stylet according to the present invention (FIG. 7); close-up, partial, longitudinal sectional, perspective view of the proximal section of the self-illuminating stylet tube shown in FIG. 7 taken through line 8-8 (FIG. 8); a close-up, partial, longitudinal sectional, perspective view of one embodiment of the intermediate section of the self-illuminating stylet shown in FIG. 7 taken through line 9-9 comprising one light transmitting element (FIG. 9); a close-up, partial, longitudinal sectional, perspective view of another embodiment of the intermediate section of the self-illuminating stylet shown in FIG. 7 taken through line 10-10 comprising two light transmitting elements (FIG. 10); and a close-up, partial, longitudinal sectional, perspective view of one embodiment of the distal section of the self-illuminating stylet shown in FIG. 7 and FIG. 9 taken through line 11-11 comprising one light transmitting element (FIG. 11). As can be seen, in one embodiment, the self-illuminating stylet 200 comprises a cylindrical body 202 comprising a proximal end 204 and a distal end 206, and extending between the proximal end 204 and the distal end 206 respectively, a proximal section 208 continuous with an intermediate section 210 continuous with a distal section 212.

In one embodiment, the cylindrical body 202 comprises transparent polyurethane, or comprises polyvinylchloride. However, the cylindrical body 202 can comprise any other material suitable for the intended purpose as will be understood by those with skill in the art with reference to this disclosure.

Figure 7:
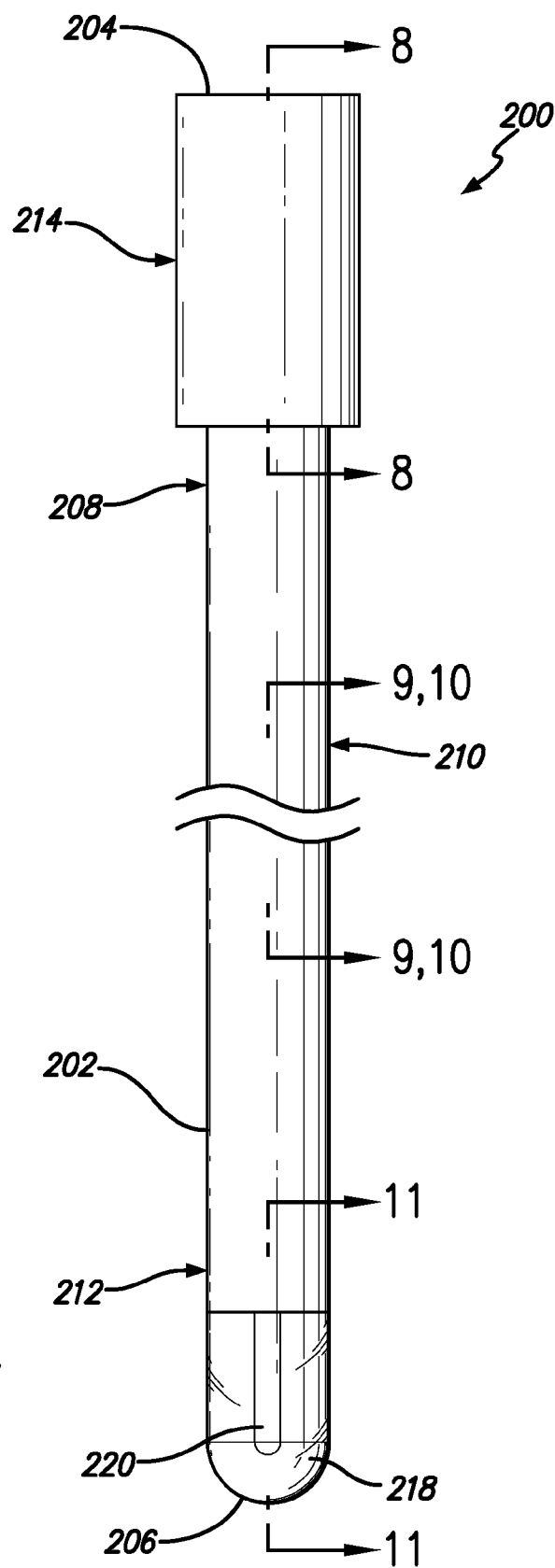
FIG. 7 is a close-up, partial, lateral perspective view of a self-illuminating stylet according to the present invention.
Figure 8:
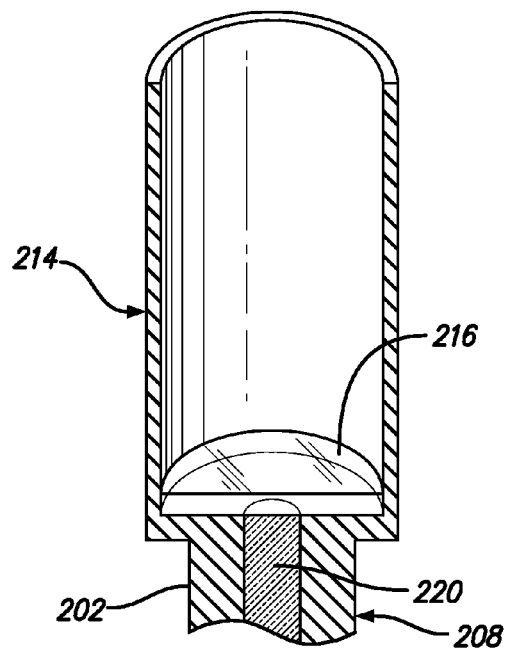
FIG. 8 is a close-up, partial, longitudinal sectional, perspective view of the proximal section of the self-illuminating stylet shown in FIG. 7 taken through line 8-8.
Figure 9:
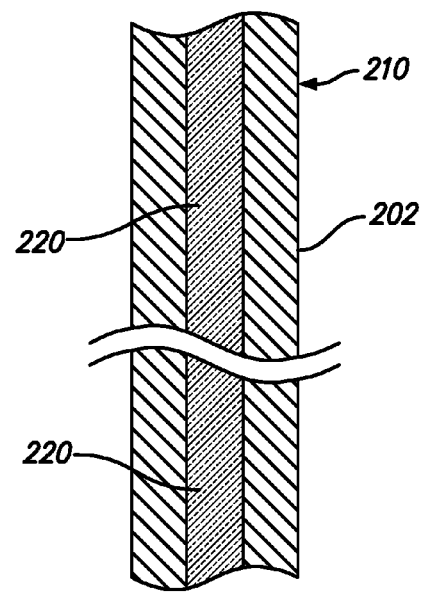
FIG. 9 is a close-up, partial, longitudinal sectional, perspective view of one embodiment of the intermediate section of the self-illuminating stylet shown in FIG. 7 taken through line 9-9 comprising one light transmitting element.

In one embodiment, the proximal section 208 of the self-illuminating stylet 200 comprises an adapter 214 for mating with a light supplying source. The adapter 214 can be a female form adapter as shown in FIG. 7 and FIG. 8, or can be a male form adapter. In one embodiment, the proximal section 208 of the self-illuminating stylet 200 further comprises a lens 216 as shown in FIG. 8 for focusing light from a light supplying source to the light transmitting element or light transmitting elements within the self-illuminating stylet 200.

The distal section 212 of the self-illuminating stylet 200 comprises a light transmitting section 218, as shown in FIG. 7 and FIG. 11, where the cylindrical body 202 is transparent or translucent sufficient to allow light from the one or more than one light transmitting element within the cylindrical body 202 to traverse the cylindrical body, and thereby to be detected, as will be understood by those with skill in the art with reference to this disclosure. In one embodiment, the light transmitting section 218 of the cylindrical body 202 of the self-illuminating stylet 200 comprises transparent polyurethane; however, the light transmitting section 218 of the self-illuminating stylet 200 can comprise any suitable material for the intended purpose as will be understood by those with skill in the art with reference to this disclosure.

The self-illuminating stylet 200 further comprises one or more than one light transmitting element 220. In one embodiment, the self-illuminating stylet 200 comprises one light transmitting element 220, as shown in FIG. 7, FIG. 8, FIG. 9 and FIG. 11. In another embodiment, the self-illuminating stylet 200 comprises two light transmitting elements 220, as shown in FIG. 10. In another embodiment, the self-illuminating stylet 200 comprises three light transmitting elements 220. In another embodiment, the self-illuminating stylet 200 comprises more than three light transmitting elements 220. Each light transmitting element 220 extends from the proximal section 208 of the self-illuminating stylet 200 within the cylindrical body 202 and terminates within the light transmitting section 218 of the distal section 212 of the self-illuminating stylet 200, as shown particularly in FIG. 7 and FIG. 11. In a preferred embodiment, each light transmitting element 220 is an optical fiber or a cable of optic fibers; however, the self-illuminating stylet 200 can comprise any suitable light transmitting element 220, as will be understood by those with skill in the art with reference to this disclosure.

According to another embodiment of the present invention, there is provided a light supplying source for use with the self-illuminating endogastric tube and the self-illuminating stylet of the present invention. Referring now to FIG. 12, FIG. 13, FIG. 14 and FIG. 15, there are shown, respectively, a lateral perspective view of a light supplying source according to the present invention (FIG. 12); a schematic view of some of the parts of the light supplying source shown in FIG. 12 (FIG. 13); a close-up, cross-sectional view of one embodiment of the light transmitting cable of the light supplying source shown in FIG. 12 and FIG. 13 taken through line 14-14 (FIG. 14); and a close-up, cross-sectional perspective view of another embodiment of the light transmitting cable of the light supplying source shown in FIG. 12 and FIG. 13 taken through line 15-15 (FIG. 15). As can be seen, in one embodiment, the light supplying source 300 comprises a light generating unit 302. In one embodiment, the light supplying source 300 further comprises a light transmitting conduit 304.

The light generating unit 302 can be any device suitable to the purpose of generating and supplying light to the one or more than one light transmitting element 148, 220 of the self-illuminating endogastric tube 100 and self-illuminating stylet 200, respectively, according to the present invention, as will be understood by those with skill in the art with reference to this disclosure. By way of example, in one embodiment the light generating unit 302 comprises a light emitting element 306 for generating light at the visible wavelengths, a filter 308 for limiting the wavelengths of light generated by the light emitting element 306, and a lens 310 for focusing the light generated by the light emitting element 306. In one embodiment, the light generating unit 302 further comprises a heat reducing element 312 for reducing the heat within the light generating unit 302 generated by the light emitting element 306.

In a preferred embodiment, the light supplying source 300 further comprises a light transmitting conduit 304. In one embodiment, the light transmitting conduit 304 is attached to the light supplying source 300. In a preferred embodiment, the light transmitting conduit 304 is connectable to the light supplying source 300, such as for example by mating with the light supplying source 300 by corresponding male/female connectors. The light transmitting conduit 304 is configured to mate with a self-illuminating endogastric tube 100 according to the present invention, or to mate with a self-illuminating stylet 200 according to the present invention, such as for example by corresponding male/female connectors. The light transmitting conduit 304 transmits light generated by the light supplying source 300 to the self-illuminating endogastric tube or to the self-illuminating stylet.

Referring now to FIG. 14 and FIG. 15, in one embodiment, the light transmitting conduit 304 comprises one or more than one light transmitting element 314. In one embodiment, each light transmitting element 314 is an optical fiber or a cable of optic fibers; however, each light transmitting element 314 can be any suitable element for the intended purpose, as will be understood by those with skill in the art with reference to this disclosure.

In one embodiment, the light transmitting conduit 304 further comprises cladding 316 surrounding each light transmitting element 314. In another embodiment, the light transmitting conduit 304 further comprises a thermoplastic buffer layer 318 surrounding each light transmitting element 314 and cladding 316. In another embodiment, the light transmitting conduit 304 further comprises a strengthening layer 320 surrounding the light transmitting element 314 and cladding 316 or surrounding the thermoplastic buffer layer 318 to impart tensile strength to the light transmitting conduit 304. In another embodiment, the light transmitting conduit 304 further comprises an outer coat 322 surrounding all of the other layers and elements of the light transmitting conduit 304, such as for example a PVC layer or a flame retardant layer. Each layer can comprise any suitable material for the intended purpose, as will be understood by those with skill in the art with reference to this disclosure.

According to another embodiment of the present invention, there is provided a method of placing an endogastric tube that does not expose the patient to ionizing radiation, or that limits the amount of ionizing radiation exposure to less than the amount associated with standard methods of placing an endogastric tube. The method comprises providing a self-illuminating stylet according to the present invention, or comprises providing a self-illuminating endogastric tube according to the present invention, or comprises providing both a self-illuminating stylet and a self-illuminating endogastric tube according to the present invention. The method comprises, first, selecting a patient who has a need that will be met by placement of an endogastric tube, such as for example a patient who needs but cannot take nutrition or medication orally, such as for example a patient with compromised mentation or a patient with a defect in swallowing.

In one embodiment, the method comprises providing a self-illuminating endogastric tube according to the present invention. Then, the distal end of the self-illuminating endogastric tube is inserted through the nasal passage or oral cavity of the patient, respectively, and into the gastrointestinal tract of the patient. Next, light is supplied to the one or more than one light transmitting element of the self-illuminating endogastric tube, causing light to be transmitted to the light transmitting section of the distal end of the self-illuminating endogastric tube. Then, the abdominal wall and the chest wall of the patient are examined to identify and locate the light from the one or more than one light transmitting element as the light passes through the body wall of the patient, where light appearing between the costal border and the umbilicus of the patient indicates placement of the distal end of the self-illuminating endogastric tube within the gastrointestinal tract of the patient, where light appearing superior to the costal border indicates incorrect placement of the distal end of the self-illuminating endogastric tube outside of the gastrointestinal tract of the patient, and where failure to identify light passing through the body wall of the patient indicates failure to confirm correct placement of the distal end of the self-illuminating endogastric tube. If light from the distal end of the self-illuminating endogastric tube appears between the costal border and the umbilicus of the patient, the placement of the distal end of the self-illuminating endogastric tube is confirmed within the gastrointestinal tract of the patient, and the self-illuminating endogastric tube is secured into position and use begun. If light from the distal end of the self-illuminating endogastric tube appears superior to the costal border, then placement of the distal end of the self-illuminating endogastric tube is proximal to the stomach of the patient, and the self-illuminating endogastric tube must be advanced further or withdrawn completely and an additional placement attempted until light from the distal end of the self-illuminating endogastric tube appears between the costal border and the umbilicus of the patient. If light from the distal end of the self-illuminating endogastric tube fails to pass through the body wall of the patient, then there is failure to confirm correct placement of the distal end of the self-illuminating endogastric tube, and the self-illuminating endogastric tube must be advanced further or withdrawn completely and an additional placement attempted until light from the distal end of the self-illuminating endogastric tube appears between the costal border and the umbilicus of the patient.

In another embodiment, the method comprises providing a self-illuminating stylet according to the present invention. Then, the distal end of the self-illuminating stylet is inserted through the nasal passage or oral cavity of the patient, respectively, and into the gastrointestinal tract of the patient. Next, light is supplied to the one or more than one light transmitting element of the self-illuminating stylet, causing light to be transmitted to the light transmitting section of the distal end of the self-illuminating stylet. Then, the abdominal wall and the chest wall of the patient are examined to identify and locate the light from the one or more than one light transmitting element as the light passes through the body wall of the patient, where light appearing between the costal border and the umbilicus of the patient indicates placement of the distal end of the self-illuminating stylet within the gastrointestinal tract of the patient, where light appearing superior to the costal border indicates incorrect placement of the distal end of the self-illuminating stylet outside of the gastrointestinal tract of the patient, and where failure to identify light passing through the body wall of the patient indicates failure to confirm correct placement of the distal end of the self-illuminating stylet. If light from the distal end of the self-illuminating stylet appears between the costal border and the umbilicus of the patient, the placement of the distal end of the self-illuminating stylet is confirmed within the gastrointestinal tract of the patient, and the self-illuminating stylet is secured into position and use begun. If light from the distal end of the self-illuminating stylet appears superior to the costal border, then placement of the distal end of the self-illuminating stylet is outside of the gastrointestinal tract of the patient, and the self-illuminating stylet must be advanced further or withdrawn completely and an additional placement attempted until light from the distal end of the self-illuminating stylet appears between the costal border and the umbilicus of the patient. If light from the distal end of the self-illuminating stylet fails to pass through the body wall of the patient, then there is failure to confirm correct placement of the distal end of the self-illuminating stylet, and the self-illuminating stylet must be advanced further or withdrawn completely and an additional placement attempted until light from the distal end of the self-illuminating stylet appears between the costal border and the umbilicus of the patient. Next, an endogastric tube is advanced over the self-illuminating stylet until the distal end of the endogastric tube is correctly placed and the self-illuminating stylet is removed leaving the endogastric tube. In one embodiment, the endogastric tube is a self-illuminating endogastric tube according to the present invention, and correct placement of the self-illuminating endogastric tube is confirmed by supplying light to the one or more than one light transmitting element of the self-illuminating endogastric tube and detecting the position of the distal end of the endogastric tube as disclosed above.

According to another embodiment of the present invention, there is provided a method of reconfirming the position of an endogastric tube that was previously placed that does not expose the patient to ionizing radiation, or that limits the amount of ionizing radiation exposure to less than the amount associated with standard methods of placing an endogastric tube, where the endogastric tube is a self-illuminating endogastric tube according to the present invention. The method comprises supplying light to the one or more than one light transmitting element of the self-illuminating endogastric tube and detecting the position of the distal end of the endogastric tube as disclosed above. In another embodiment, the method comprises inserting a self-illuminating stylet according to the present invention into the endogastric tube and advancing the distal end of the self-illuminating stylet to the distal end of the endogastric tube, and then supplying light to the one or more than one light transmitting element of the self-illuminating stylet and detecting the position of the distal end of the endogastric tube as disclosed above. As will be understood by those with skill in the art with reference to this disclosure, this latter method of reconfirming the position of an endogastric tube that was previously placed is useful if the self-illuminating aspect of the self-illuminating endogastric tube ceases to work while the self-illuminating endogastric tube is being used within a patient.

According to another embodiment of the present invention, there is provided a kit for placing the distal end of an endogastric tube within the gastrointestinal tract of a patient, where the kit comprises a self-illuminating stylet, or comprises a self-illuminating endogastric tube, or comprises both a self-illuminating stylet and a self-illuminating endogastric tube as disclosed in this disclosure.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A kit comprising:
a stylet comprising:
a cylindrical body comprising a proximal section and a distal section, the cylindrical body having a length and formed without a lumen and having no openings, the proximal section of the cylindrical body being opaque, the distal section of the cylindrical body comprising a closed terminal end portion comprising a light transmission section extending entirely around a circumference of the cylindrical body; the light transmission section comprising a transparent or translucent material; and
a plurality of light transmitting elements extending through the cylindrical body and terminating in the light transmission section, each of the light transmitting elements comprising an optical fiber through which a light source can transmit light from the proximal section to the distal light transmission section; and
an endogastric tube comprising:
a tubular body comprising a non-transparent proximal section and a distal section, the distal section comprising:
a closed terminal distal end formed without a lumen and being weighted; and
a light transmission window located proximal to the terminal distal end and distal to the proximal section, the window extending completely around the circumference of the tubular body and being formed with a lumen;
the proximal section of the tubular body having a lumen extending through the proximal section of the tubular body and terminating in the transmission window, the stylet being placed within the lumen and having a length which registers the light transmission section of the stylet adjacent the light transmission window of the tubular body of the endogastric tube, whereby light from the light source transmits light in all directions from the light transmission window of the endogastric tube.

2. The kit of claim 1, wherein the endogastric tube further comprises a plurality of light transmitting elements disposed in a tubular wall of the tubular body.

3. The kit of claim 2, wherein each of the light transmitting elements of the endogastric tube comprises an optical fiber.

4. The kit of claim 2, wherein each of the light transmitting elements of the endogastric tube extends from the proximal section of the endogastric tube and terminates in the transmission window.

5. The kit of claim 1, wherein the endogastric tube further comprises an opening in a lateral wall of the tubular body, the opening positioned between the light transmission window and the closed terminal distal end.

6. The kit of claim 1, where the proximal section of the endogastric tube further comprises a side extension comprising an accessory lumen.

7. The kit of claim 6, wherein the endogastric tube further comprises a cap configured to seal the accessory lumen.

8. The kit of claim 1, wherein the endogastric tube is an enteric tube.

9. The kit of claim 1, wherein the endogastric tube is a nasogastric tube.

10. The kit of claim 1, wherein the endogastric tube is an orogastric tube.

11. A method of introducing an endogastric tube into a patient, the method comprising:
inserting a stylet into an endogastric tube, the stylet comprising:
a cylindrical body comprising a proximal section and a distal section, the cylindrical body having a length and formed without a lumen and having no openings, the proximal section of the cylindrical body being opaque, the distal section of the cylindrical body comprising a closed terminal end portion comprising a light transmission section extending entirely around a circumference of the cylindrical body; the light transmission section comprising a transparent or translucent material; and
a plurality of light transmitting elements extending through the cylindrical body and terminating in the light transmission section, each of the light transmitting elements comprising an optical fiber through which a light source can transmit light from the proximal section to the distal light transmission section;
the endogastric tube comprising:
a tubular body comprising a non-transparent proximal section and a distal section, the distal section comprising:
a closed terminal distal end formed without a lumen and being weighted; and
a light transmission window located proximal to the terminal distal end and distal to the proximal section, the window extending completely around the circumference of the tubular body and being formed with a lumen;
the proximal section of the tubular body having a lumen extending through the proximal section of the tubular body and terminating in the transmission window;
advancing the stylet into the endogastric tube until the light transmission section of the stylet is adjacent to the light transmission window of the tubular body of the endogastric tube;
inserting both the stylet and the endogastric tube through a nasal passage or oral cavity of the patient and into a gastrointestinal tract of the patient;
illuminating the plurality of light transmitting elements, wherein during the illumination of the plurality of light transmitting elements, light from the light source transmits light in all directions from the light transmission window of the endogastric tube;
examining the abdominal wall and the chest wall of the patient to locate the light and determine proper placement of the endogastric tube within the gastrointestinal tract, wherein light appearing between the costal border and the umbilicus of the patient indicates proper placement of the distal end of the endogastric tube within the gastrointestinal tract of the patient, and wherein light appearing superior to the costal border indicates incorrect placement of the distal end of the endogastric tube outside of the gastrointestinal tract of the patient; and
removing the stylet from the patient.

12. The method of claim 11, wherein determining proper placement of the endogastric tube is performed without exposing the patient to ionizing radiation.

13. The method of claim 11, wherein after determining incorrect placement of the distal end of the endogastric tube, further advancing or withdrawing the endogastric tube until the light appears between the costal border and the umbilicus of the patient.

14. The method of claim 11, further comprising, after removing the stylet from the patient, reconfirming the position of the endogastric tube by:
   inserting the stylet into the endogastric tube;
   illuminating the plurality of light transmitting elements of the stylet; and
   examining the abdominal wall and the chest wall of the patient to locate the light and determine proper placement of the endogastric tube.

15. The method of claim 11, wherein reconfirming the position of the endogastric tube is performed without exposing the patient to ionizing radiation.

16. The method of claim 11, wherein the endogastric tube further comprises a plurality of light transmitting elements disposed in a tubular wall of the tubular body.

17. The method of claim 16, further comprising:
   illuminating the plurality of light transmitting elements of the endogastric tube; and
   examining the abdominal wall and the chest wall of the patient to locate the light of the endogastric tube and determine proper placement of the endogastric tube.

18. The method of claim 17, wherein light of the endogastric tube appearing between the costal border and the umbilicus of the patient indicates proper placement of the distal end of the endogastric tube within the gastrointestinal tract of the patient, and wherein light of the endogastric tube appearing superior to the costal border indicates incorrect placement of the distal end of the endogastric tube outside of the gastrointestinal tract of the patient.

* * * * *